United States Patent [19]
Satoh et al.

[11] Patent Number: 5,245,189
[45] Date of Patent: Sep. 14, 1993

[54] INFRARED OPTICAL ELEMENT AND METHOD OF MAKING THE SAME

[75] Inventors: Shuichi Satoh; Yasushi Goda; Kazuwo Tsuji, all of Itami, Japan

[73] Assignee: Sumitomo Electric Industries, Ltd., Osaka, Japan

[21] Appl. No.: 851,942

[22] Filed: Mar. 13, 1992

[30] Foreign Application Priority Data

Mar. 14, 1991 [JP] Japan .................................. 3-75621
Apr. 25, 1991 [JP] Japan .................................. 3-124847

[51] Int. Cl.$^5$ ............................ G02B 1/02; G02B 1/00
[52] U.S. Cl. .................................... 250/343; 356/244; 359/356
[58] Field of Search ............................ 250/343, 348.1; 356/244, 246; 359/356, 642, 900; 51/283 R, 284 R

[56] References Cited

U.S. PATENT DOCUMENTS

| | | | |
|---|---|---|---|
| 3,860,399 | 1/1975 | Noble et al. | 51/283 R |
| 4,776,223 | 10/1988 | Moss | 356/244 X |
| 4,864,778 | 9/1989 | Smith | 51/283 R |
| 4,910,403 | 3/1990 | Kilham et al. | 250/243 |
| 4,970,396 | 11/1990 | Wong | 356/244 X |
| 4,972,630 | 11/1990 | Seki et al. | 51/283 R |

*Primary Examiner*—Paul M. Dzierzynski
*Assistant Examiner*—Edward J. Glick
*Attorney, Agent, or Firm*—Wenderoth, Lind & Ponack

[57] ABSTRACT

An infrared optical part comprised of a synthetic diamond single crystal, and a method of making the same. The infrared optical part is comprised of a synthetic diamond having a nitrogen content of not more than 5 ppm and a boron content of not more than 3 ppm, wherein the parallelism between its light incident and reflecting surfaces is not more than one minute. The infrared optical part is used as a window member in infrared spectral analysis. It is also used in the form of a pair of anvils for holding a sample therebetween in connection with the measurement of transmitted light that has passed through the sample after the sample is compressed. The part is also used in the form of an infrared ATR prism. The method involves the steps of abrading an infrared optical part having the above mentioned nitrogen and boron content by a grinder, measuring the parallelism between the light incident and reflecting surfaces of the part by laser light, and smoothing the grinding apparatus, whereby the parallelism is set to a level of not more than $2.91 \times 10^{-4}$ radians.

4 Claims, 4 Drawing Sheets

INFRARED OPTICAL ELEMENT AND METHOD OF MAKING THE SAME

BACKGROUND OF THE INVENTION

1. Field of the Invention

The present invention relates to an infrared optical part for use mainly in infrared spectral analysis, and a method of making the same.

2. Description of the Prior Art

Example uses for infrared optical parts in infrared spectral analysis include use as a window member for infrared spectral analysis, uses as an anvil in organic-material absorption spectrum measurement, and use in infrared ATR prisms.

In infrared spectral analysis, a window member is required for the following purposes, among others: (1) to isolate the detector and/or light source from the external environment, for which purpose the window member is used as, for example, a bolometer window member, a vacuum window member, a dust- and sand-proof window member, or an acid- and alkali-resistant window member; (2) to measure the absorption spectrum or emission spectrum of a sample under special environmental conditions, for which purpose the window member is used as, for example, a cryostat window member, a vacuum-chamber window member, a pressure-cell window member, or a compression window member; and (3) to hold samples in a measuring operation.

Infrared optical materials useful in making such window members include KBr, ZnSe, GaAs, Ge (Miyata, T., "Development of Transparent Optical Parts for High Power $CO_2$ Laser").

Natural diamond of the IIa type which involves no nitrogen absorption in the infrared region is also used for such window members. However, such diamond available is mostly smaller than 3 mm in diameter and practically little or no supply of such diamond of 5 mm in diameter or more has been obtainable, because the output of a natural IIa type diamond is limited to such a small proportion as 1 to 2%, it being very rare that such diamond is obtained in a relatively large single-crystal size.

The characteristics of the above exemplified conventionally used materials and the problems thereof are shown in Table 1. It can be seen from Table 1 that natural IIa type diamond is characteristically most advantageous; however, the problem is that such diamond is actually unobtainable in any large crystal size.

Hitherto, measurement of the absorption spectrum has been carried out in the following two ways:

(1) A sample is powdered, and mixed and diluted with a material, such as KRS-5, which absorbs no energy in the infrared region, and the same is sintered into a test specimen by hot pressing or otherwise. The test specimen is subjected to measurement by an infrared spectro-analytical apparatus. FIG. 5 is an explanatory view illustrating such method of infrared spectral analysis, in which the test specimen, designated by numeral 41, is placed on a sample holding stage 43 and exposed to a measuring light 42 incident from the light source for spectral measurement by a detector with respect to the transmitted light 44 which has passed through the test specimen. A reflector mirror is shown by the manual 45.

(2) A laminated sample is placed between a pair of opposed diamond anvils processed so as to be able to bear pressure and is crushed the application of pressure into film shape so that it can readily transmit light. The test piece, thus prepared, is subjected to measurement. In this method of measurement, a diamond of the so-called IIa type which has a nitrogen content of 1 ppm or less is selectively used. This way of measurement is schematically illustrated in FIG. 6, in which numeral 51 designates a test piece held between opposed diamond anvils 52, 52, numeral 53 designates an anvil holder, 54 designates a pressing screw, and 55 designates a measuring light beam incident from the light source. The incident light 55 is transmitted by the test piece 51 after being refracted by a reflector mirror 56 and focusing mirrors 57. Again, the light is refracted by another focusing mirror 57 before it is sensed as transmitted light 58 by a detector used for the absorption spectral measurement.

Of these conventional methods, the method described under item (2) is more commonly employed, but this method has the disadvantages as described below.

(1) Since a natural IIa type diamond, the output of which is extremely small, is used, the method is limited in that only a small sized anvil could be used. Therefore, when normal infrared-spectral measuring light (of 2.5–3.0 mm in diameter) is made incident upon a sample, the sample portion, which is of no more than 0.5 mm in diameter, can provide only a limited transmittance of 1/25 to 1/36 of the intensity, it being thus impossible to obtain any proper spectral measurement.

As such, it is necessary to focus the incident light first on the sample portion so that the light which has passed through the sample portion is made into parallel light rays, and then to cause the parallel light rays to be sensed by the detector or to be again focused on the detector, in order to reasonably prevent any loss of incident light intensity. For carrying out this method, a precision-made and expensive optical system is required.

(2) A local portion on which light rays are focused is observed. Unlike any absorption spectrum employed

TABLE 1

| Characteristic Material | Transmission region (μm) | Refractive index at 10.6 μm | Thermal conductivity W/cmk | Problem |
| --- | --- | --- | --- | --- |
| Ge | 1.8–13 | 4.02 | 0.59 | Transmission region narrow |
| CdTe | 0.9–13 | 2.69 | 0.06 | Toxicity and low thermal conductivity |
| GaAs | 0.9–18 | 3.30 | 0.48 | Transmission region narrow |
| ZnSe | 0.5–22 | 2.40 | 0.18 | Transmission region narrow, liable to damage |
| KBr | 0.2–30 | 1.54 | 0.048 | Deliquescent, liable to damage |
| KCl | 0.2–24 | 1.47 | 0.065 | Deliquescent, liable to damage |
| KRS-5 | 0.5–40 | 2.38 | 0.054 | Deliquescent, soft, toxic |
| Nat. IIa diamond | 0.25– | 2.38 | 20.0 | Almost unavailable in large size | over an entire test specimen, the absorption spectrum thus obtained may provide erroneous information.

(3) Natural IIa type diamond is expensive and its supply is unstable.

(4) It is desirable to use a diamond anvil which is pressure resistant and has a face (100). However, the orientation of the planes of natural IIa type diamond is not clear because it has a curved surface. This makes it difficult to produce a diamond anvil with a face orientation of (100), which is highly resistant to pressure, into exact coincidence with the surface of the sample which is subjected to pressure.

In conventional method of making infrared optical parts, as FIG. 4 shows a, cast disc 1 on the surface of which abrasive grains of diamond have been applied is driven into high speed rotation by a motor 2 and a rotating belt 3. The work 5 to be abraded is set in a fixing jig 4, with a load adjustably applied by weight 6, one end of the jig 4 being placed on table 7; and the work 5 is subjected to abrasion by being pressed against the cast disc 1.

This method involves the following difficulties.

(1) Parallelism cannot be measured during the process of abrading. This makes it necessary to remove the work 5 from the jig 4 to check for parallelism checking and, after parallelism is measured, it is reset in position. In this case, some positional deviation may occur and, as a consequence, the workpiece cannot be set in the desired angular position.

(2) Diamond is so hard that the cast disc 1 is abraded in conjunction with the work. In this case, the cast disc 1 may not uniformly be abraded. Therefore, the desired parallelism cannot be achieved.

(3) Since a large surface area is subject to abrasion, a large load is required. Therefore, a large load is applied to the jig 4, which results in some deformation. As a consequence, the desired parallelism cannot be obtained.

SUMMARY OF THE INVENTION

Accordingly, it is a first object of the present invention to provide an infrared optical part having excellent optical characteristics which is made of a synthetic diamond having a lower nitrogen content and a lower boron content than usually used and has a parallelism of $2.91 \times 10^{-4}$ radians.

It is a second object of the present invention to provide an infrared optical part having excellent optical characteristics for use as a window member which is made of a synthetic diamond having a nitrogen content of not more than 5 ppm and a boron content of not more than 3 ppm in the crystal structure thereof, selected from large-size synthetic diamonds.

It is a third object of the present invention to provide an infrared optical part which is so designed that, in the process of measuring the absorption spectra of organic matter, absorption spectral incident light rays are made incident directly on a test piece held between diamond anvils, without the light rays being gathered, so that the transmitted light can be measured without provision of any focusing system, and which permits the use of large synthetic diamond single crystals and thus solves the problem of diamond supply.

It is a fourth object of the present invention to provide a method of making an infrared optical part, wherein during the grinding operation, the grinder is constantly subjected to dressing (smoothing) while the parallelism of the test piece is measured, whereby a high parallelism of the order of not more than $2.91 \times 10^{-4}$ radians can be attained which could not be achieved by conventional techniques.

The above and other objects and features of the present invention will be more fully apparent from a consideration of the following description taken in connection with the accompanying drawings, which are given by way of example.

DETAILED DESCRIPTION OF THE INVENTION

Figure 1:
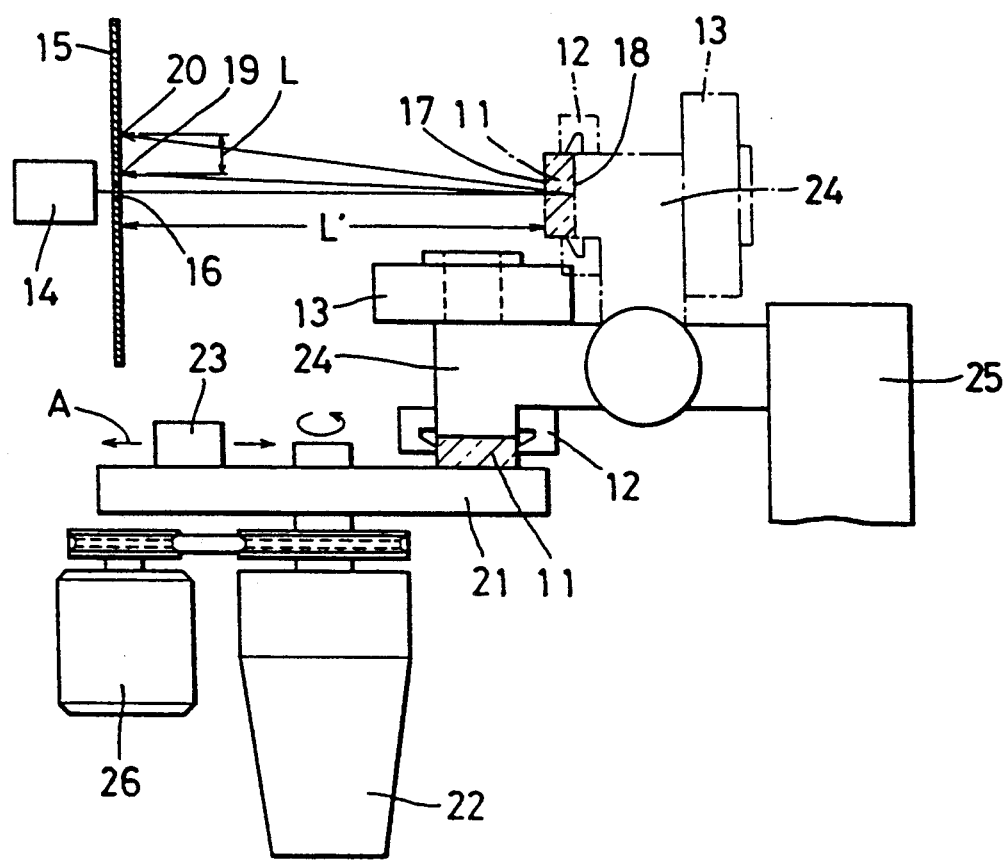
FIG. 1 is a side view showing a processing apparatus according to the invention.

According to a first aspect of the invention, there is provided an infrared optical part comprised of a synthetic diamond single crystal having a nitrogen content of not more than 5 ppm and a boron content of not more than 3 ppm and wherein the parallelism between its surface of incidence of light for measurement and its reflective surface with respect to the light is not more than $2.91 \times 10^{-4}$ radians.

The effect of selecting one having a nitrogen content of not more than 5 ppm in its crystal structure from large-size synthetic diamonds will be explained below.

Single crystal diamond of the IIa type which involves no infrared absorption in the infrared region usually accounts for only 1-2% of the output of natural diamond and, as a matter of fact, there exists no diamond of such size as 6 mm in diameter or more which can be used in this first aspect of the invention. Therefore, it is necessary that a large-size synthetic diamond of the IIa type be used. The primary feature of this first aspect of the invention is that it teaches the use of a synthetic diamond having a nitrogen content of not more than 5 ppm is suitable for use as a window member. In synthetic diamonds, nitrogen is present in the form of nitrogen atoms scattered in an isolated form among the carbon atoms. If a nitrogen atom having one more electron than a carbon atom is included in the crystal structure, the crystal configuration changes to a zinc blend structure, so that a sharp absorption peak occurs at 7.51 μm and a strong absorption having a gently-sloping peak at 8.85 μm occurs. These absorption peaks unfavorably affect the of spectral analysis process for the following reasons.

(1) A sharp peak at 7.51 μm cannot be eliminated where FTIR (Fourier transform infrared spectrometer) is employed. and it appears as a pseudo peak in a sample, which leads to an erroneous measurement result.

(2) A strong absorption having a gently-sloping peak at 8.84 μm lowers the (transmitted light)/(incident light) ratio and decreases the S/N ratio, thus resulting in increased measurement errors.

According to the invention, where the nitrogen content in the crystal structure is not more than 5 ppm, the synthetic diamond can be satisfactorily used as a window member without involving these problems.

Nextly, the effect of selecting a synthetic diamond having a boron content of not more than 3 ppm will be explained.

In synthesizing a synthetic diamond, ferrous catalysts, such as Fe, Co, and Ni, are used in which boron is always present as an impurity. Boron has a sharp absorption at 3.41 $\mu$m, 3.56 $\mu$m, 4.07 $\mu$m, and 7.51 $\mu$m, which appear as pseudo peaks in the sample, and this leads to an erroneous measurement result. Especially when such material is cooled, the peaks become sharper and more intense and are separated into several parts, so that the material cannot be used as a window member as for a cryostat. According to the invention, the effect of such boron peaks is eliminated when the boron content of the crystal is not more than 3 ppm.

The effect of surface parallelism on an infrared optical part used as a window member will be explained.

When such part is used as a large-size window member, parallelism has an important bearing upon the measurement results for the following reasons.

(1) In infrared measurements (and in the case of FTIR in particular), interference by light, incident on the window member, and also by reflection of the transmitted light, poses a problem. Poor parallelism is a cause of interference which leads to an error in intensity measurements. Interference occurs at spots $\frac{1}{2}\lambda$, $\frac{1}{4}\lambda$, $\frac{1}{8}\lambda$, and $\frac{1}{2^n}\lambda$ distant from the surface of perfect parallelism. Since the reflectivity of diamond is of the order of 30%, the intensity of interference is about 10% at $\frac{1}{2}\lambda$, and about 0.8% at $\frac{1}{4}\lambda$. Therefore, in order that a part may be used at least as a window member, it is necessary that the parallelism of this part be $\frac{1}{4}\lambda$ or less of the diameter. Since infrared light is normally used at a wave length of more than 2.5 $\mu$m, in the case of window member of 8 mm dia., $\theta = \tan^{-1}(2.5 \mu m / 8 mm) = 3.2 \times 10^{-4}$ radians. Therefore, a parallelism of not more than one minute is required.

(2) Where a window member is used, the optical path of the measuring light becomes longer and, if poor parallelism is involved, the optical axis of the focusing system does not coincide with the optical axis of the measuring light, with the result that the quantity of light that enters the detector is decreased. In this case, the required parallelism of the window member varies according to the type of optical system, the type of detector, and the number of window members used. However, where an average type instrument is employed, it is necessary that two window members 1 be used for an optical path of 600 mm to control the deviation in optical axis within the limits of ±0.5 mm. For this purpose, parallelism $\theta$ per piece is expressed by the following equation:

$$2 \times \theta = \tan^{-1}\frac{0.5}{600} \quad \theta = 4.07 \times 10^{-4} \text{ radians}$$

Therefore, it is required that parallelism per piece be not more than $4.07 \times 10^{-4}$ radians.

As stated earlier, the parallelism of a large-size window member must be within $2.91 \times 10^{-4}$ radians.

According to the second aspect of the present invention there is provided an infrared optical part useful for absorption spectral measurements with respect to organic matter, which will be explained below.

Figure 2:
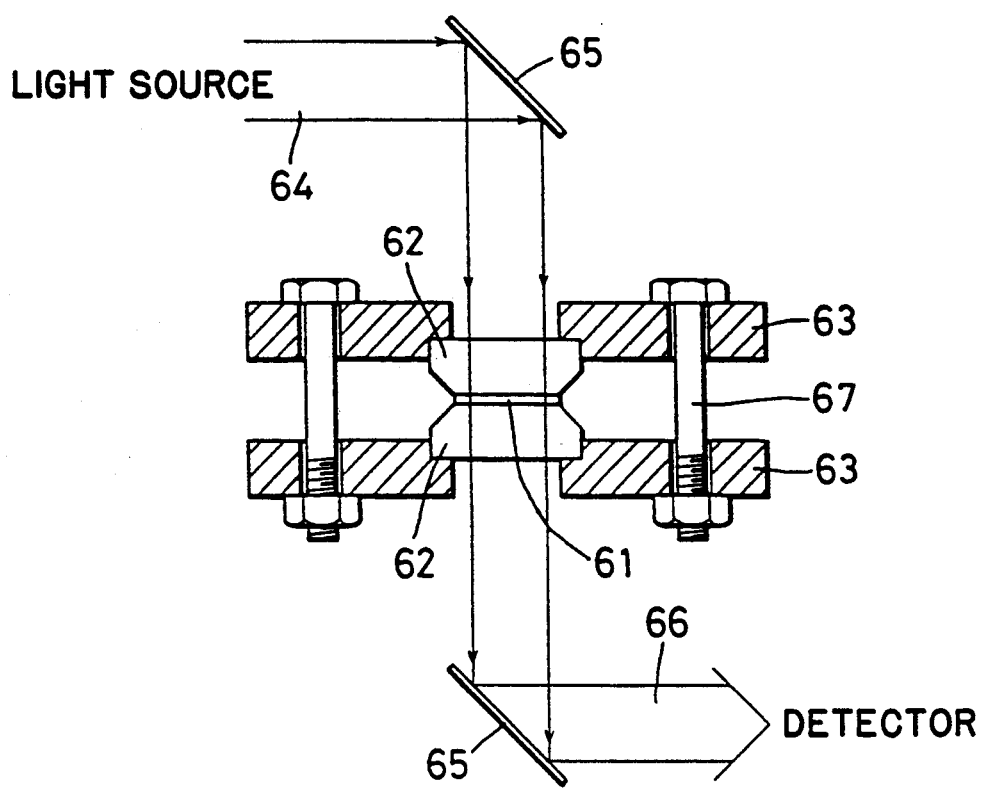
FIG. 2 is an explanatory view showing, by way of example, a method of an infrared analysis in which an anvil of infrared synthetic diamond according to the invention is employed.

The infrared optical part in accordance with this second aspect of the invention is so designed that where pieces of synthetic diamond are used as a pair of opposed anvils between which is placed a test sample, the measuring infrared light may be made incident on the sample, after the sample has been subjected to pressure, without the step of light focusing being required, so that the light which has passed through the sample can be directly measured for absorption spectral measurement with respect to the sample. The mode of carrying out this process is shown in FIG. 2.

As shown, infrared light 64 from the light source, after being refracted by a reflector mirror 65, becomes incident directly upon a sample 61 held between opposed anvils 62, 62 comprised of synthetic diamond which are supported by anvil support blocks 63, 63, and transmitted light 66 that has passed through the sample is measured by a detector (not shown). The numeral 67 represents a pressure screw.

Referring further to this second aspect of the invention, pieces of synthetic diamond are used as anvils in view of the fact that the availability of IIa type single-crystal diamond, that absorbs no energy in the infrared region, accounts for only 1-2% of the output of natural diamond, which proportion becomes extremely smaller when larger single crystal diamonds are used.

Diamond anvils used in the invention must be of 3 mm in diameter or more, because measuring infrared light rays, as in FTIR measurement, usually have a diameter of the order of 2.5-3 mm in diameter, in view of which an anvil diameter of not less than 3 mm in diameter is needed to transmit all infrared light rays without the step of focusing being required.

In view of the extremely limited production of natural IIa type diamond as stated above, it is impossible to obtain an industrial-scale supply of anvils of not less than 3 in diameter made from rough diamond of the natural IIa type. According to a second aspect of the invention, synthetic diamond anvils of not less than 3 mm in diameter are employed, whereby the above-mentioned problem of diamond supply has been solved.

Another advantage of the use of synthetic diamond for anvils is that, since the orientation of the crystal growth is definite, a (100) oriented face that is highly resistant against compression can easily be determined for use as a compression surface for a sample. Where natural diamond is used, it is necessary that crystal orientation must be previously measured by a tridimensional X-ray goniometer or the like, which is very troublesome.

According to this aspect of the invention, the nitrogen content of the synthetic diamond used as anvils is not more than 5 ppm and the boron content of the synthetic diamond is not more than 3 ppm, as is the case with the earlier described window member. If nitrogen atoms having one more electron than carbon atoms are isolatedly scattered in the crystal structure, new absorption will occur in the near-ultraviolet and infrared regions.

In the infrared region, an intense absorption having a gently-sloping large peak at 8.85 $\mu$m and a sharp peak at 7.51 $\mu$m does occur. The absorption coefficient in such phenomenon becomes greater in proportion to the nitrogen content. The sharp peak at 7.51 $\mu$m is a problem in infrared spectro-chemical analysis as in FTIR (Fourier transform spectroscopic instrument) measurements. In the case of FTIR measurements, gently-sloping peaks can be removed by virtue of Fourier transformation, but sharp peaks cannot be eliminated.

According to the invention, when the nitrogen content is not more than 5 ppm, such peaks as mentioned above present no problem in spectral measurements. In the near ultraviolet region in the vicinity of 293 nm, a sharp peak occurs due to absorption by Ib type nitrogen, which phenomena seldom occurs with natural diamond, because the output of Ib type rough stone is as low as 0.2% of that of natural diamond production. Further, production of natural diamond that can satisfy the conditions, wherein the nitrogen content is not more than 5 ppm as defined in the invention is practically zero as already stated.

In cathode luminescence measurements with natural IIa type diamond, a peak occurs at 400–450 nm, whereas in the case of synthetic diamond no luminescence can be seen in the above-mentioned range and, instead, a peak occurs at 470–530 nm, which peak does not occur with IIa type natural diamond.

Even where the difference between natural IIa type diamond and the synthetic diamond used in the invention cannot be determined by infrared absorption spectral analysis, the difference can be found by carrying out the above-mentioned near-ultraviolet absorption and cathode luminescence measurement.

Further, according to the invention, the parallelism between the sample setting face of the anvils and the plane of infrared light incidence or the plane of infrared light transmission is $2.91 \times 10^{-4}$ radians or less. It has been found that use of large-sized diamond anvils gives rise to several inconveniences unless some improvement is achieved in respect of the parallelism between the sample setting face of the anvils and the plane of infrared light incidence or the plane of transmission, over conventional small-type anvils (in which the parallelism has been $1.45 \times 10^{-3}$ radians or less). The following facts have been discovered.

(1) Since a sample is compressed to 2-10-odd $\mu$m, the diamond anvils come into into contact with each other or local stress concentration may occur to cause damage to the anvils per se, unless parallelism between the surface of the upper anvil and the sample setting surface of the lower anvil is set at $2.91 \times 10^{-4}$ radians or less.

(2) Where the anvils are employed in an FTIR, interference between the sample setting surface and the opposite surface of the anvils, a problem is posed. Such interference is likely to occur at spots $\frac{1}{2}\lambda$, $\frac{1}{4}\lambda$, $\frac{1}{8}\lambda$, and $\frac{1}{2^n}\lambda$ apart from the plane of perfect parallelism. Since the reflectivity of diamond is of the order of 30%, the degree of interference at $\frac{1}{4}\lambda$ is not more than 0.8%, which poses no problem, but interference at $\frac{1}{2}\lambda$ is a problem. Therefore, it is desired that parallelism should be less than $\frac{1}{2}\lambda$ ($\lambda = 2.5$ $\mu$m) relative to the length of the measurement surface, which corresponds to about $5.82 \times 10^{-4}$ or less.

(3) Since no optical system for focusing is employed, no change in the optical path of measuring light is effected by the infrared diamond anvils and the entire light rays must be made incident into the detector. To this end, it is preferred that the angle of deviation between the optical axes of the incident light and the transmitted light be set to be within $1.16 \times 10^{-3}$ radians.

According to a third aspect of the invention, there is provided an infrared optical part in which the nitrogen content and boron content are of almost equivalent weight and electrically neutralized, the effect of which will be described below.

This infrared optical part is comprised of a synthetic diamond single crystal having nitrogen and boron contents of almost equivalent weight, which are electrically neutralized, such that the coefficient of absorption in the infrared region, at 8.85 $\mu$m, 3.41 $\mu$m, 5.56 $\mu$m, 4.07 $\mu$m, and 7.51 $\mu$m, is 0.1 cm$^{-1}$ or less.

Most of the absorption by nitrogen atoms are removed through the aforesaid electric neutralization, and yet a slight residue is present in the diamond.

Absorption of light by such residual nitrogen atoms occurs at 8.85 $\mu$m.

Also, absorption by boron atoms remaining in the crystal occurs at 3.41 $\mu$m, 4.07 $\mu$m, 3.56 $\mu$m and 7.51 $\mu$m.

Insofar as the nitrogen content and boron content are not more than 5 ppm and not more than 3 ppm, respectively, there is no problem from the standpoint of practical use. However, if it is desired that the coefficient of absorption be further decreased, an n-type impurity of nitrogen and a p-type impurity of boron should be equalized in weight. By so doing, there will occur electric neutralization (AD pair), which will result in a deceased dipole moment and reduced absorption.

Relative proportions of impurities are preferably 1–5 ppm of nitrogen and 1–3 ppm of boron.

The aforementioned phenomenon of electrical neutralization can be ascertained by the following method.

The presence of an AD pair can be determined by the intensity of cathode luminescence.

A wide band of luminescence is observed over a wavelength range of 400–500 nm, which is proportional to the equalized weight of nitrogen and boron. The presence of an AD pair can also be determined by a phenomenon such that an increase in electric resistance occurs upon heating. A resistance of $1 \times 10^8$ $\Omega$.cm can be observed until a temperature of about 500° C. is reached, but as the temperature rises, the resistance will tend to decrease.

Some particular examples are given to further illustrate this third aspect of the invention. In the examples, an ATR prism is used as an infrared optical part, but it is noted that comparable effects can be obtained with other optical parts.

In producing infrared ATR prisms (attenuated total reflectance prisms), the nitrogen content of the crystal was varied by changing the kind of solvent used. Boron was added in an amount of 3 ppm. A single crystal of 12 mm square was grown on a seed crystal of 5 mm dia. by the temperature gradient method under a super-high pressure of 5.5 GPa at 1300° C. The amount of boron contained in the crystal was varied within the range of 0 to 3 ppm.

Subsequently, the crystal was processed into a prism having a surface for incident light, angled at 45° according to the processing method of the invention. This will be described in detail hereinafter.

Parallelism measurements indicated that the parallelism between the surface for incidence and the reflecting surface and that between opposed surfaces for sample placement were within $2.91 \times 10^{-4}$ radians.

Measured characteristics of these prisms are shown, together with those of a comparative example, in Table 2.

TABLE 2

| | Experiment No. | | |
|---|---|---|---|
| | 1 | 2 | 3 |
| Synthetic | Fe - 55 Co - | Fe - 55 Co - | Fe - 55 Co - |

TABLE 2-continued

|  | Experiment No. | | |
| --- | --- | --- | --- |
|  | 1 | 2 | 3 |
| solvent (wt %) | 0.4 Al - 4.5 C | 1.0 Al - 4.5 C | 1.5 Al - 4.5 C |
| Nitrogen content (ppm) | 10 | 3 | 1.5 |
| Boron content (ppm) | 3 | 3 | 3 |
| Absorption coefficient at 8.85 μm | 0.2 | zero | 0.04 |
| Absorption coefficient at 3.41 μm at 3.56 μm at 4.07 μm at 7.51 μm | zero | zero | nearly zero |
|  | Comparative Example | Example | Example |

According to a fourth aspect of the invention, there is provided a method of making the above-described infrared optical parts of the invention, which will be described below.

The method of the invention comprises the steps of abrading an infrared optical part of the above-described synthetic diamond single crystal by a grinder, measuring the parallelism between the light incident and reflecting surfaces of the part by laser light, and smoothing the grinder, whereby the parallelism is set to a level of not more than $2.91 \times 10^{-4}$ radians.

Figure 4:
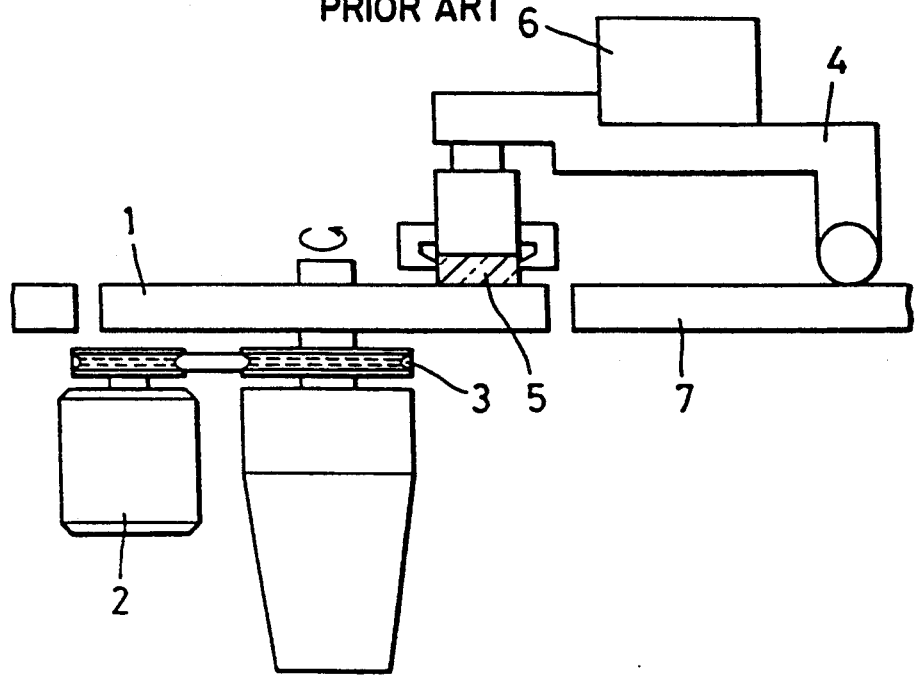
FIG. 4 is a side view showing a conventional processing apparatus.
Figure 5:
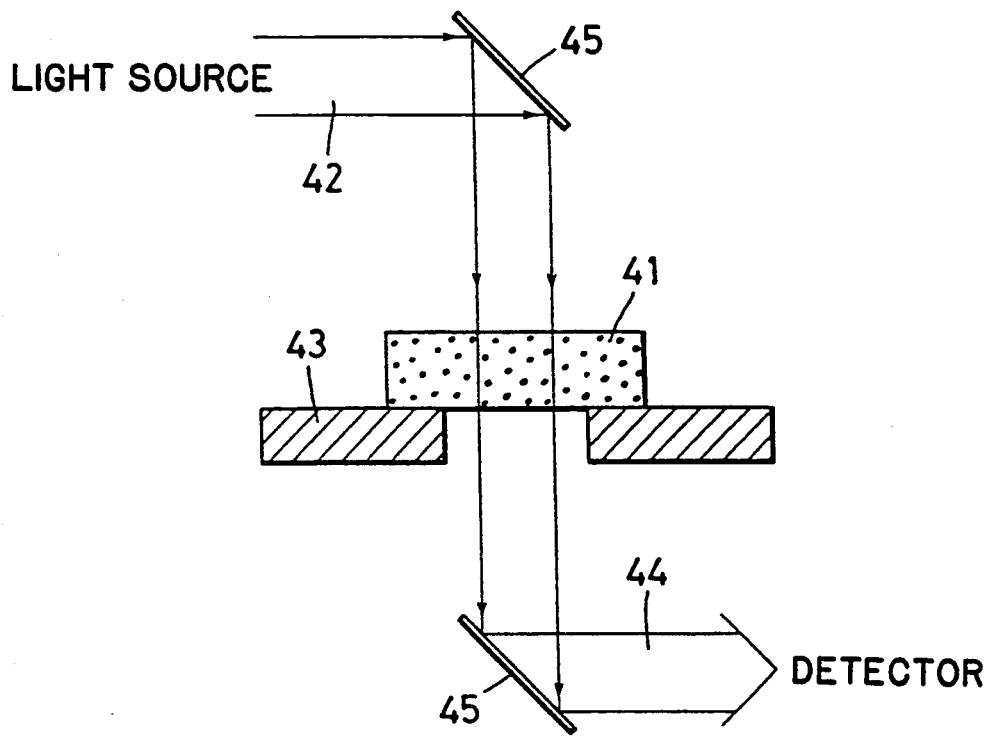
FIG. 5 is an explanatory view showing a conventional method of infrared analysis.
Figure 6:
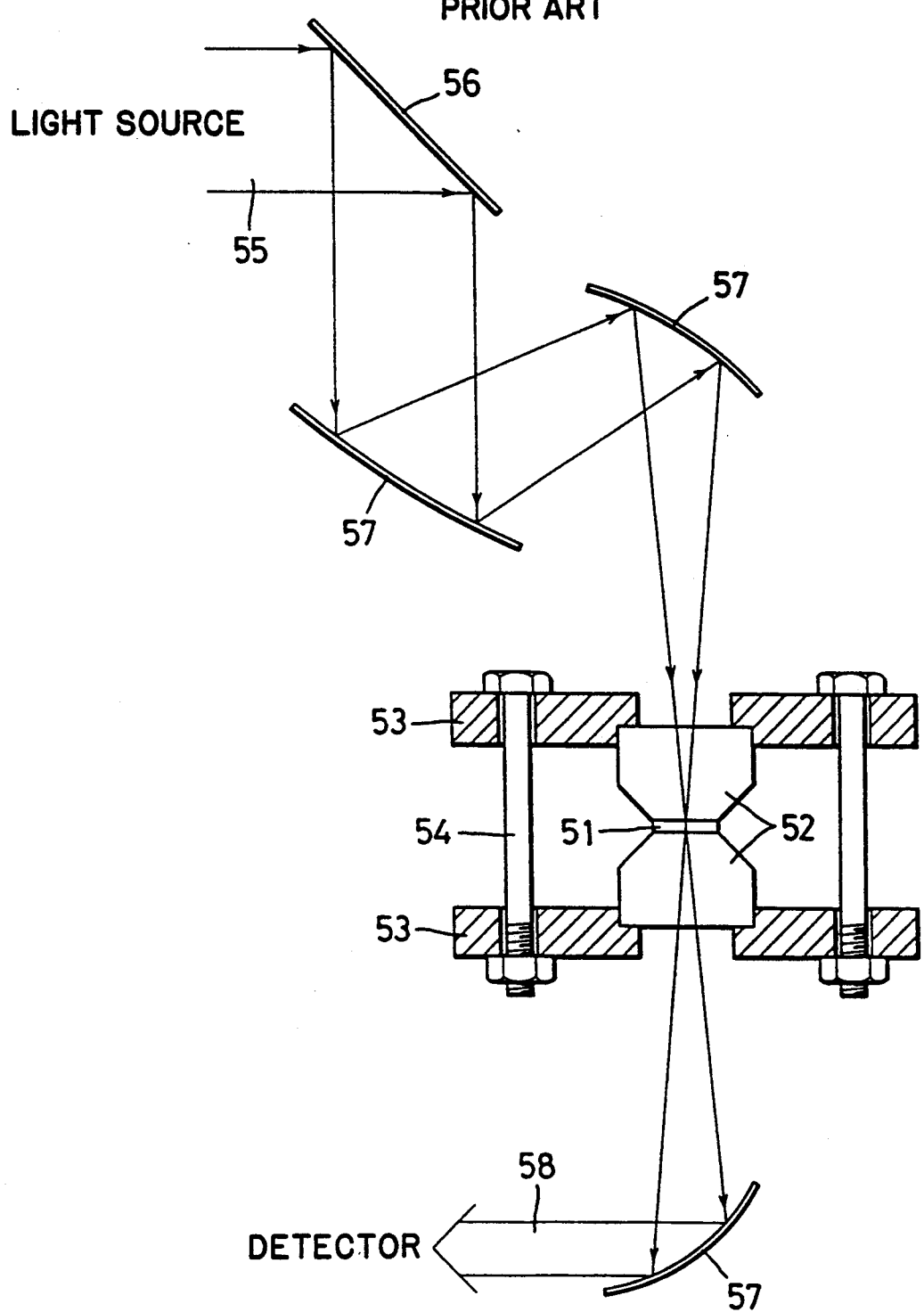
FIG. 6 is an explanatory view showing the method of infrared analysis in which a conventional diamond anvil is employed.

According to the conventional method shown in FIG. 4, as earlier stated, (1) a workpiece 5 is once removed from the jig 4 for to measure parallelism, because parallelism cannot be measured during the stage of grinding. After the parallelism measurement has been carried out, the workpiece 5 is again set in position. In this case, some angular deviation may occur and the workpiece fails to be set within the desired angular range. (2) Diamond is so hard that cast iron plate 1 is forced to be also abraded but not uniformly. As a consequence, workpiece 5 is abraded while being held in tilted condition, so that the desired parallelism cannot be obtained. (3) Since the workpiece is abraded over a large area, a considerable load is required; therefore, a large load is exerted on the jig 4, and some deformation to the jig, occurs so that the desired parallelism cannot be attained.

In order to solve these problems, according to the fourth aspect of the invention, laser beam reflection is utilized to permit the measurement of parallelism while the workpiece is set in the jig.

The method will be described in detail with reference to FIG. 1.

Workpiece 11, as set in fixing jig 12, is swung up from a position at which it is in contact with case iron plate 21 to undergo the process of abrading, as shown in FIG. 1. The alternate long and short dash line shows a grinding head 24 as swung up for the measurement of parallelism. The surface of workpiece 11 in the swung-up position is exposed to a beam from an He-Ne laser 14 that is passed through slit 16. Reflected light from surface 17 gives a reflection dot 19 on measuring plate 15. Reflected light from the back 18 of workpiece 11 gives a reflection dot 20 on the measuring plate 15. The parallelism between the workpiece surface 17 and the back 18 is measured on the basis of the distance L between the reflection dots 19 and distance L' between slit 16 and workpiece surface, and thickness of the workpiece.

In this case, dresser 23 is slid in the diametrical direction shown by arrow A so as to allow the surface of the cast iron plate 21 to be kept even. Also, for the purpose of measuring parallelism, the grinding head 24 and fixing table 25 are designed to be of increased rigidity so that possible deformation due to the weight of spindle 13 can be minimized.

The following examples 1 to 3 are given to further illustrate the method of the invention.

EXAMPLE 1

In order to make infrared window members, a single crystal of 10 mm square was grown on a seed crystal of 4 mm in diameter by varying the type of solvent each case and by employing the temperature differential technique under a super high pressure of 5.4 GPa at 1280° C. The nitrogen content was varied between 0.3–20 ppm. The single crystal was worked to the size of 10 mm in diameter × thickness 1.5 mm so that a parallelism of not more than $2.91 \times 10^{-4}$ radians can be obtained. Each diamond disc thus obtained was used as a window member for an organic material processing cell, and absorption spectrum measurement was made with respect thereto employing FTIR. The results are shown in Table 3.

TABLE 3

|  | Experiment No. | | | |
| --- | --- | --- | --- | --- |
|  | 1 | 2 | 3 | 4 |
| Synthetic solvent (wt %) | Fe - 40 Co 4 Al - 4.5 C | Fe - 40 Co - 0.81 Al - 4.5 C | Fe - 40 Co - 0.4 Al - 4.5 C | Fe - 40 Co - 0.24 Al - 4.5 C |
| Nitrogen content (ppm) | 0.3 | 5 | 9 | 20 |
| Single crystal weight (carat) | 9.5 | 9.0 | 9.2 | 8.9 |
| Peak at 7.51 μm | Nil | Nil | Some | Some |
| Suitability for use as window member | Good | Good | Unsuitable because of pseudo peaks | Unsuitable because of pseudo peaks and poor S/N ratio |
|  | Example | Example | Comparative Example | Comparative Example |

It can be seen that from Table 3 that a synthetic diamond having a nitrogen content of not more than 5 ppm is most suitable. An attempt was made to obtain a natural IIa type diamond of 10 carat class in order to make a window member of 10 mm in diameter × thickness 1.5 mm of IIa natural diamond, but such diamond could not be obtained. It is noted that measurement of the nitrogen concentration in the crystal was effected by using the ESR (electron spin resonance) technique.

EXAMPLE 2

In order to make a cryostat window member, a large single crystal of 10 carat class was synthesized from a seed crystal of 4 mm in diameter by employing the temperature differential method under a super high pressure of 5.5 GPa at 1250° C. When synthesized, the boron present as an impurity in the solvent material is entrapped the crystal. Since a cryostat is employed at very low temperature, a pseudo-absorption peak due to boron appears. This peak is small when the cryostat is employed at room temperature. In view of this fact, the effect of a boron absorption peak on infrared measurement was examined by varying the solvent material and the impurity boron content. The results are shown in Table 4.

TABLE 4

| | Experiment No. | | | |
|---|---|---|---|---|
| | 5 | 6 | 7 | 8 |
| Solvent composition (wt %) | Fe - 60 Co - 1.5 Al - 4.5 C | Fe - 60 Co - 1.5 Al - 4.5 C | Fe - 60 Co - 1.5 Al - 4.5 C | Fe - 60 Co - 1.5 Al - 4.5 C |
| Impurity boron in material (ppm) | 1 ppm (material A) | 15 ppm (material B) | 25 ppm (material C) | 50 ppm (material D) |
| Boron content of single crystal (ppm) | 0.2 | 3 | 5 | 10 |
| Boron absorption peak at 3.41 μm, etc. | Nil | Nil | Slight | Yes |
| Suitability for window member | Good | Good | Unsuitable because of pseudo peaks | Unsuitable because of pseudo peaks |
| | Example | Example | Comparative Example | Comparative Example |

It can be seen from Table 4 that a synthetic diamond having a boron content of not more than 3 ppm in its crystal structure is suitable for use as window member. It is noted that the amount of boron in the solvent was measured by chemical analysis of the material dissolved in acid. The amount of boron in the crystal structure was measured by employing a secondary ion mass spectroscopy (SIMS).

EXAMPLE 3

Abrading was carried out by employing the method according to the invention as shown in FIG. 1, in order to obtain a parallelism of not more than $2.91 \times 10^{-4}$ radians. For comparison purposes, abrading was also carried out according to the conventional method as shown in FIG. 4. In the present example, the rough stone subjected to abrasion was a synthetic diamond of 10 carat class which was prepared by using a solvent composed of Fe—40% Co—12% Al—4.4% C under a super high pressure of 5.5 GPa at 1290° C., and a single crystal of 3.5 mm in diameter as a seed crystal. The nitrogen content of the crystal was 0.6–1.0 ppm, and the boron content was 0.1–0.3 ppm. Parallelism measurement was made at three spots including the center of the disc and two opposed circumferential spots (A and B). The method used for parallelism measurement was the same as that shown in FIG. 1, except that the distance between the slit and workpiece was increased to three times and that measurement was made in a dark room, whereby measurement accuracy was enhanced. The results are shown in Table 5.

TABLE 5

| | Experiment No. | | | |
|---|---|---|---|---|
| | 9 | 10 | 11 | 12 |
| Abrading method | Invention | Invention | Prior Art | Prior Art |
| Abraded surface | (100) | (110) | (100) | (110) |
| Parallel (min.) Center | 0.25 | 0.18 | 3.11 | 4.06 |
| Circumf. A | 0.75 | 0.44 | 5.20 | 5.34 |
| Circumf. B | 0.53 | 0.62 | 4.81 | 4.67 |
| | Example | Example | Comparative Example | Comparative Example |

As can be seen from Table 5, according to the method of the invention, a parallelism of less than $2.91 \times 10^{-4}$ radians been obtained with respect to not only the abraded surface but to the entire disc surface as well.

EXAMPLE 4

Figure 3:
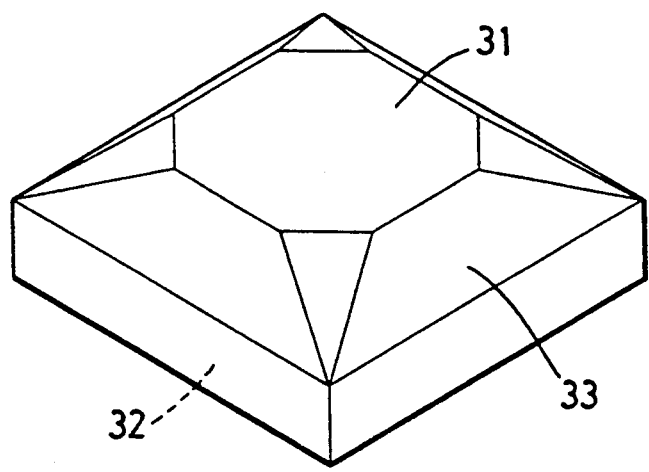
FIG. 3 is a schematic view of the diamond anvil in FIG. 2.

In order to make infrared diamond anvils, synthetic diamonds having a nitrogen content of 0.2 to 15 ppm were produced by varying the kind of synthetic solvent as shown in Table 6 and by employing the temperature differential method under a super high pressure of 5.5 GPa at 1300° C. The boron content of the synthetic diamond was 1 ppm. Each synthetic diamond thus obtained was worked to a configuration having a sample setting surface 31, infrared light incident surface or transmission surface 32, and a pressure reinforced surface 33 as shown in FIG. 3. Each pair of the anvils, thus made, were set to a holding jig according to the combinations set out in Table 6. Then, a piece of silicon rubber in thin leaf form was compressed between the anvils, and absorption spectral measurements were made employing an FTIR infrared spectroscope.

Any pair with respect to which a sharp peak attributable to the nitrogen content of the diamond was observed at 7.51 mm in the spectrum was judged unacceptable. The results are shown in Table 6. It is noted that an ESR (electron spin resonance) measuring device was used for measurement of the boron content of the diamond single crystal. Absorption spectra were observed with all the silicon rubber pieces, and in Table 6, pairs used in Experiment Nos. 7 and 8 (combination D), in particular, were found to be of small S/N ratio, with poor measurement accuracy.

TABLE 6

| | Example | | | | Comparative Example | | | |
|---|---|---|---|---|---|---|---|---|
| | 1 | 2 | 3 | 4 | 5 | 6 | 7 | 8 |
| Synthetic solvent (wt %) | Fe - 40% Co - 4% Al | Fe - 40% Co - 4% Al | Fe - 40% Co - 0.8% Al | Fe - 40% Co - 0.8% Al | Fe - 40% Co - 0.5% Al | Fe - 40% Co - 0.5% Al | Fe - 40% Co - 0.3% Al | Fe - 40% Co - 0.3% Al |
| Nitrogen content (ppm) | 0.2 | 0.3 | 5 | 4 | 7 | 8 | 12 | 15 |
| Weight (carat) | 1.6 | 1.5 | 1.3 | 1.5 | 1.4 | 1.5 | 1.6 | 1.6 |
| Combination No. of opposed anvils | A | A | B | B | C | C | D | D |

TABLE 6-continued

| | Example | | | | Comparative Example | | | |
|---|---|---|---|---|---|---|---|---|
| | 1 | 2 | 3 | 4 | 5 | 6 | 7 | 8 |
| Peak at 7.51 μm | nil | nil | nil | nil | slight | slight | yes | yes |

EXAMPLE 5

Ten pieces of rough stones of 1.3 to 1.7 carat were made using a solvent of Fe—60% Co—1.5% Al, 5.4 GPa at 1280° C. Of these pieces of rough stones, five were subjected to abrading by the grinder shown in FIG. 1 in order that they may be abraded to a parallelism of not more than $2.9 \times 10^{-4}$ radians. For comparison purposes, the remaining five rough stones were abraded according to the conventional method in which a cast iron plate and a grinding jig were used. The results are shown in FIG. 7. Measurement of post-abrasion parallelism was made in accordance with the laser reflection method as shown in FIG. 1, except that the distance L' between the slit and the workpiece was increased to three times and that measurement was accurately done on an anti-vibration table in a dark room. The abraded surface was varied among three crystal faces, (100), (110), and (112), from one to another, in order to examine how such variation will be reflected in the degree of parallelism obtained. Further, it is noted that pairs of anvils required for infrared absorption spectral measurement were employed in varied combinations, namely A (as in Nos. 1 and 2 in Table 6), B (as in Nos. 3 and 4 in Table 6), C (as in Nos. 5 and 6 in Table 6), and D (as in Nos. 7 and 8), in order to examine the effect of the nitrogen content.

TABLE 7

| | Example | | | | | Comparative Example | | | | |
|---|---|---|---|---|---|---|---|---|---|---|
| | 11 | 12 | 13 | 14 | 15 | 16 | 17 | 18 | 19 | 20 |
| Abrading method | FIG. 1 | FIG. 1 | FIG. 1 | FIG. 1 | FIG. 1 | Prior art | Prior art | Prior art | Prior art | Prior art |
| Abraded face | (100) | (100) | (100) | (110) | (112) | (100) | (100) | (100) | (110) | (112) |
| Parallelism (min.) | 1.00 | 0.54 | 0.77 | 0.82 | 0.98 | 4.15 | 3.02 | 2.29 | 5.08 | 3.47 |

It can be seen from Table 7 that whereas a parallelism of not more than $2.91 \times 10^{-4}$ radians was attained with respect to all the five samples worked by the FIG. 1 grinder of the invention, the parallelism measurements with respect to the other five samples worked by the conventional grinding method did not come up to the target level of parallelism, with a variation range of from $5.82 \times 10^{-4}$ radians to $1.45 \times 10^{-3}$ radians. However, in neither case, was there found any particular difference in parallelism which was attributable to the difference in the abraded crystal surface.

As stated above, according to the method of the invention it has now become possible to obtain infrared optical parts of infrared diamond single crystal which have hitherto been unobtainable. Furthermore, the effect of nitrogen and boron concentrations on the optical characteristics of such parts have now been clarified, and it has become possible to work such parts to a high degree of parallelism. As a result, it is now possible to obtain infrared optical parts of diamond having stable optical characteristics.

It has also been found that when infrared optical parts worked according to the method of the invention were employed, absorption spectra with respect to the entirety of each sample can be easily and accurately measured at low cost, without the necessity of using such particular light-focusing system as in shown in FIG. 3.

What is claimed is:

1. An infrared optical element having parallel opposed surfaces comprised of a synthetic diamond single crystal having a nitrogen content of not more than 5 ppm and a boron content of not more than 3 ppm and wherein the parallelism between said opposed surfaces, on which an infrared measurement beam transmits or reflects, is not more than $2.91 \times 10^{-4}$ radians.

2. An infrared optical element as defined in claim 1 wherein said infrared optical element is a diamond optical anvil, which makes it possible to measure a sample without a step of focusing light being required, so that the light which has passed through the sample can be directly measured.

3. An infrared optical element as defined in claim 1, wherein the nitrogen content and boron content of said infrared optical element are of almost equivalent weight and are electrically neutralized so that the coefficient of absorption in the infrared region, at 8.85 μm, 3.41 μm, 3.56 μm, 4.07 μm, and 7.51 μm, is 0.1 cm$^{-1}$ or less.

4. A method of making a synthetic diamond infrared optical element having parallel opposed surfaces which comprises the steps of abrading a synthetic diamond single crystal having a nitrogen content of not more than 5 ppm and a boron content of not more than 3 ppm by a grinding apparatus, measuring the parallelism between said opposed surfaces of said abraded synthetic diamond by laser light, and smoothing said grinding apparatus, whereby said parallelism of said infrared optical element is set to a level of not more than $2.9 \times 10^{-4}$ radians.

* * * * *